United States Patent [19]

Fielding

[11] 4,380,539
[45] Apr. 19, 1983

[54] NEMATOCIDAL COMPOSITION CONTAINING O,O-DIETHYL O-(5-PHENYLISOXAZOL-3-YL)PHOSPHOROTHIOATE AND AN ETHANIMIDOTHIOATE

[75] Inventor: Max J. Fielding, Wilmington, Del.

[73] Assignee: E. I. Du Pont de Nemours and Company, Wilmington, Del.

[21] Appl. No.: 242,583

[22] Filed: Mar. 11, 1981

[51] Int. Cl.³ .................... A01N 43/80; C07D 261/12
[52] U.S. Cl. ..................................... 424/200; 548/117
[58] Field of Search ......................................... 424/200

[56] References Cited
U.S. PATENT DOCUMENTS
3,759,941 9/1973 Sampei et al. ..................... 424/200

*Primary Examiner*—Anton H. Sutto

[57] ABSTRACT

A method of protecting plants from plant parasitic nematodes is provided. This method comprises applying to the locus of nematode infestation a plant protective amount of a mixture consisting essentially of A. O,O-diethyl O-(5-phenylisoxazol-3-yl)phosphorothioate, and
B. at least one of:
  (1) methyl N-[[(methylamino)carbonyl]oxy]ethanimidothioate,
  (2) methyl 2-(dimethylamino)-N-[[(methylamino)carbonyl]oxy]-2-oxoethanimidothioate; and
  (3) 2-methyl-2-(methylthio)propionaldehyde O-methylcarbamoyloxime, the weight ratio of A to B being in the range of about 1:10 to about 10:1, preferably about 2:1 to about 3:1.

4 Claims, No Drawings

NEMATOCIDAL COMPOSITION CONTAINING O,O-DIETHYL O-(5-PHENYLISOXAZOL-3-YL)PHOSPHOROTHIOATE AND AN ETHANIMIDOTHIOATE

BACKGROUND OF THE INVENTION

1. Field of Invention

This invention relates to methods of protecting plants from plant parasitic nematodes and more particularly to such methods using a synergistic combination of compounds.

2. Prior Art

Plant-parasitic nematodes are unsegmented worms, largely under one-eighth of an inch in length. Most species occur in soil and many of them attack the roots and other underground parts of plants. Some, on the other hand, attack the crown, stem, leaves, buds or seeds of plants.

Plant-parasitic nematodes damage crops and reduce yields of useful produce in several ways. Some species, termed "ectoparasites," attack plants largely from the outside. Their feeding often results in the death of the rootlets involved. When the numbers of such nematodes are large, many rootlets are killed, and crops suffer by correspondingly reduced growth and limited yields. Other species, termed "endoparasites," enter and live within the root tissue. Both ectoparasitic and endoparasitic nematodes may cause the death of the tissue surrounding the point of attack as well as malformation of the plant part involved. Such effects not only reduce the general vigor of the plant, but, in many cases, actually destroy the market value of the produce (such as malformed carrots). Furthermore, damage caused by plant-parasitic nematodes may serve as entry points for other plant pathogens such as fungi, bacteria and viruses.

Crop losses in the United States alone due to plant-parasitic nematodes are estimated to be in the range of one-half to one billion dollars annually.

The two basic methods available for avoiding or mitigating nematode damage to crops are to increase fertilizer and water to offset stunted root systems or to apply chemicals to control the nematodes. The first method is expensive and only partially effective, especially when the nematode causes malformation of the produce. The second method, while more effective, has been hampered by the lack of suitable chemicals. Many of the chemicals now available for nematode control are exceedingly phytotoxic and therefore unsuitable for use on growing crops. Others are unpleasant to handle, temporary in action or excessively expensive.

SUMMARY OF THE INVENTION

According to the present invention there is provided a method of protecting plants from plant parasitic nematodes comprising applying to the locus of nematode infestation a plant protective amount of a mixture consisting essentially of:

A. O,O-diethyl O-(5-phenylisoxazol-3-yl)phosphorothioate, and

B. at least one of:
 (1) methyl N-[[(methylamino)carbonyl]oxy]ethanimidothioate,
 (2) methyl 2-(dimethylamino)-N-[[(methylamino)carbonyl]oxy]-2-oxoethanimidothioate; and
 (3) 2-methyl-2-(methylthio)propionaldehyde O-methylcarbamoyloxime, the weight ratio of A to B being in the range of about 1:10 to about 10:1.

DETAILED DESCRIPTION OF THE INVENTION

It has been discovered that a combination of compounds known in the agricultural chemical art provides synergistic control of nematodes when applied to the nematodes or to the site of their infestation.

Compound A contained in the mixture used in the present invention (O,O-diethyl O-(5-phenylisoxazol-3-yl)phosphorothioate) has the formula:

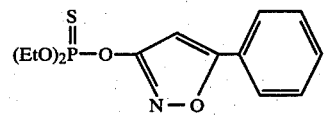

This compound and other related compounds and their use as insecticides are described in South African Pat. No. 4958/66 (U.S. equivalent U.S. Pat. No. 3,759,941). This reference also describes insecticidal combinations with "carbamate insecticides." Compound A can be prepared as described in this reference.

Compound B(1) which can be contained in the mixture used in the present invention (methyl N-[[(methylamino)carbonyl]oxy]ethanimidothioate) has the formula:

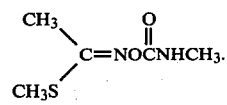

This compound, combinations of these compounds with other pesticides, related compounds and their use as insecticides are described in U.S. Pat. Nos. 3,576,834 and 3,639,633. The use of these compounds to control nematodes is described in U.S. Pat. No. 3,459,866. Compound B(1) can be prepared as described in U.S. Pat. No. 3,576,834 or 3,639,633.

Compound B(2) which can be contained in the mixture used in the present invention (methyl 2-(dimethylamino)-N-[[(methylamino)carbonyl]oxy]-2-oxoethanimidothioate) has the formula:

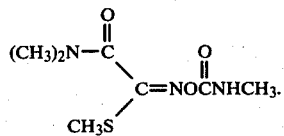

This compound and related compounds are described in U.S. Pat. No. 3,658,879 and U.S. Pat. No. 3,530,220 as nematicides, insecticides and acaricides. Compound B(2) can be prepared as described in these patents.

Compound B(3) which can be contained in the mixture used in the present invention (2-methyl-2-(methylthio)propionaldehyde O-methylcarbamoyloxime) has the formula:

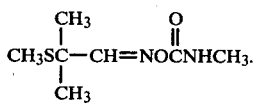

This compound and related compounds are described in U.S. Pat. No. 3,217,037. Compund B(3) can be prepared as described in this patent.

A preferred mixture is compound A and compound B(1) in a weight ratio of about 2:1 to about 3:1.

The mixtures useful in the present invention have shown greater than additive control of plant parasitic nematodes, such as Southern root-knot nematode (*Meloidgyne incognita*) when applied in weight ratios of A to B from about 1:10 to about 10:1, preferably about 2:1 to about 3:1. These mixtures are well suited to the control of plant parasitic nematodes inhabiting soil in which plants are planted or to be planted. The physical nature of these mixtures permit their movement deep into undisturbed soil around plant roots. The safety margin for plants make practical such applications as well as applications to soil being prepared for planting.

Use rates for application to soil in which plants are growing are generally the same as for application to soil being prepared for planting. Such rates range from about 0.125 to 50 kg of active ingredients per hectare of surface actually treated. Rates of 0.25 to 20 kilograms per hectare are most preferred for these uses for reasons of convenience and economy.

Other methods of applying the mixtures useful in this invention to prevent the destructive effects of plant-parasitic nematodes include: spraying above-ground parts such as stems, leaves or buds in which nematodes are present, dipping or soaking reproductive parts such as seeds, potato, cane pieces, slips or bulbs in a water suspension, solution or emulsion of the active ingredients. The rates of active ingredients in the sprays or dips are in the range of 30 grams to 1.2 kilograms per 100 liters.

Representative nematodes from which the mixtures useful in this invention offer protection are the following:

Awl nematode—*Dolichodorus heterocephalus*
Banana nematode—*Pratylenchus musicola*
Bud and leaf nematodes—Aphelenchoides spp.
Burrowing nematode—*Radopholus similis*
Carrot root nematode—*Heterodera carotae*
Coffee root-knot nematode—*Meloidogyne exigua*
Corn nematode—*Pratylenchus zeae*
Dagger nematodes—Xiphinema spp.
Golden nematode—*Globodera rostochiensis*
Grass nematode—*Anguina agrostis*
Lance nematodes—Hoplolaimus spp.
Lesion nematodes—Pratylenchus spp.
Northern root-knot nematode—*Meloidogyne hapla*
Pea root nematode—*Heterodera gottingiana*
Peanut root-knot nematode—*Meloidogyne arenaria*
Pin nematodes—Pratylenchus spp.
Potato rot nematode—*Ditylenchus destructor*
Reniform nematode—*Rotylenchulus reniformis*
Rice nematode—*Ditylenchus angustus*
Ring nematodes—Criconemoides spp.
Smooth-headed lesion nematode—*Pratylenchus brachyurus*
Southern root-knot nematode—*Meloidogyne incognita*
Soybean cyst nematode—*Heterodera glycines*
Spiral nematodes—Helicotylenchus spp.
Stem and bulb nematode—*Ditylenchus dipsaci*
Stine nematodes—Belonolaimus spp.
Stubby-root nematodes—Trichodorus spp.
Sugar beet nematode—*Heterodera schachtii*
Tobacco cyst nematode—*Heterodera tabacum*
Tobacco stunt nematode—*Tylenchorhynchus claytoni*
Wheat nematode—*Anguina tritici*

The synergistic properties of mixtures useful in this invention were discovered in the following greenhouse tests.

EXAMPLE 1

Pots containing soil infested with the Southern root-knot nematode (*Meloidogyne incognita*) were treated with a mixture of two parts by weight of compound A (O,O-diethyl O-(5-phenylisoxazol-3-yl)phosphorothioate) and one part by weight of compound B(1)—methyl N-[[(methylamino)carbonyl]oxy]ethanimidothioate at rates of 5, 3, 1, 0.5, 0.25 and 0.125 kilograms (active ingredients) per hectare. Methyl N-[[(methylamino)carbonyl]oxy]ethanimidothioate alone, and O,O-diethyl O-(5-phenylisoxazol-3-yl)phosphorothioate alone were also applied at the above rates by mixing in the soil. Untreated infested soil was included for comparison. Cucumber seeds were planted and grown in treated and untreated soil under normal greenhouse conditions. After two weeks the roots were examined for nematode attack and the following observations were made on nematode control (Table I).

TABLE I

| Treatment | kg/ha Active Ingredient | % Nematode Control (Average 5 Replicates) |
|---|---|---|
| A 2 parts B(1) 1 part | 5.000 | 100% |
| | 3.000 | 100% |
| | 1.000 | 96% |
| | 0.500 | 78% |
| | 0.250 | 38% |
| | 0.125 | 0% |
| B(1) | 5.000 | 100% |
| | 3.000 | 100% |
| | 1.000 | 100% |
| | 0.500 | 78% |
| | 0.250 | 38% |
| | 0.125 | 0% |
| A | 5.000 | 78% |
| | 3.000 | 34% |
| | 1.000 | 0% |
| | 0.500 | 0% |
| | 0.250 | 0% |
| | 0.125 | 0% |
| Untreated Control | — | 0% |

At the lower rates, it is obvious that the combination has more than additive effect in the control of root-knot nematode.

EXAMPLE 2

Pots containing soil infested with the Southern root-knot nematode (*Meloidogyne incognita*) were treated with a mixture of three parts by weight of compound A (O,O-diethyl O-(5-phenylisoxazol-3-yl)phosphorothioate) and one part by weight of compound B(2)—methyl 2-(dimethylamino)-N-[[(methylamino)carbonyl]oxy]-2-oxoethanimidothioate at rates of 1 and 0.5 kilogram (active ingredients) per hectare. Methyl 2-(dimethylamino)-N-[[(methylamino)carbonyl]oxy]-2-oxoethanimidothioate alone, at rates of 0.25 and 0.125 kilogram per hectare, and O,O-diethyl O-(5-phenylisoxazol-3-yl)phosphorothioate alone at 0.75 and 0.375 kilogram per hectare were also applied by mixing in the soil. Untreated infested soil was included for comparison. Cucumber seeds were planted and grown in treated and untreated soil under normal greenhouse conditions. After two weeks the roots were examined for nematode attack and the following observations were made on root-knot nematode control (Table II).

TABLE II

| Treatment | kg/ha Active Ingredient | % Nematode Control (Average 5 Replicates) |
|---|---|---|
| A 3 parts B(2) 1 part | 1.000 | 94% |
|  | 0.500 | 84% |
| B(2) | 0.250 | 88% |
|  | 0.125 | 48% |
| A | 0.750 | 0% |
|  | 0.375 | 0% |
| Untreated Control | — | 0% |

The 0.5 kg/ha rate of the mixture contains 0.125 kg/ha of compound B(2) and 0.375 kg/ha of compound A. This combination is almost twice as active on root-knot nematode as one would predict from adding the results obtained from each chemical alone. The high application rate of compound B(2) alone is quite effective; therefore, the effects of the combination are not as readily apparent as in Example 1.

EXAMPLE 3

Pots containing soil infested with the Southern root-knot nematode (Meloidogyne incognita) were treated with a mixture of two parts by weight of compound A (O,O-diethyl O-(5-phenylisoxazol-3-yl)phosphorothioate) and one part by weight of compound B(1)—methyl N-[[(methylamino)carbonyl]oxy]ethanimidothioate at rates of 1 and 0.5 kilograms (active ingredients) per hectare. Methyl N-[[(methylamino)carbonyl]oxy]ethanimidothioate alone was tested at rates of 0.33 and 0.166 kilogram per hectare by mixing in the soil. O,O-diethyl O-(5-phenylisoxazol-3-yl)phosphorothioate alone was tested at rates of 0.66 and 0.33 kilogram per hectare by mixing in the soil. Untreated infested soil was included for comparison. Cucumber seeds were planted and grown in treated and untreated soil under normal greenhouse conditions. After two weeks the roots were examined for nematode attack and the following observations were made on nematode control (Table III).

TABLE III

| Treatment | kg/ha Active Ingredient | % Nematode Control (Average 5 Replicates) |
|---|---|---|
| A 2 parts B(1) 1 part | 1.000 | 86% |
|  | 0.500 | 46% |
| B(1) | 0.33 | 26% |
|  | 0.166 | 0% |
| A | 0.66 | 0% |
|  | 0.33 | 0% |
| Untreated Control | — | 0% |

It is obvious that the combination has more than additive effect in the control of root-knot nematode.

FORMULATIONS

Useful formulations of the mixtures useful in the invention can be prepared in conventional ways. They include dusts, granules, pellets, solutions, suspensions, emulsions, wettable powders, emulsifiable concentrates and the like. Many of these may be applied directly. Sprayable formulations can be extended in suitable media and used at spray volumes of from a few pints to several hundred gallons per acre. High strength compositions are primarily used as intermediates for further formulation. The formulations, broadly, contain about 1% to 99% by weight of active ingredient(s) and at least one of (a) about 0.1% to 20% surfactant(s) and (b) about 5% to 99% solid or liquid diluent(s). More specifically, they will contain these ingredients in the following approximate proportions:

|  | Percent by Weight* | | |
|---|---|---|---|
|  | Active Ingredient(s) | Diluent(s) | Surfactant(s) |
| Wettable Powders | 20–90 | 0–74 | 1–10 |
| Oil Suspensions, Emulsions, Solutions, (including Emulsifiable Concentrates) | 5–50 | 40–95 | 0–15 |
| Aqueous Suspension | 10–50 | 40–84 | 1–20 |
| Dusts | 1–25 | 70–99 | 0–5 |
| Granules and Pellets | 1–95 | 5–99 | 0–15 |
| High Strength Compositions | 90–99 | 0–10 | 0–2 |

Lower or higher levels of active ingredient can, of course, be present depending on the intended use and the physical properties of the compounds. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Ed., Dorland Books, Caldwell, N.J. The more absorptive diluents are preferred for wettable powders and the denser ones for dusts. Typical liquid diluents and solvents are described in Marsden, "Solvents Guide," 2nd Ed., Interscience, New York 1950. Solubility under 0.1% is preferred for suspension concentrates; solution concentrates are preferably stable against phase separation at 0° C. "McCutcheon's Detergents and Emulsifiers Annual", Allured Publ. Corp., Ridgewood, N.J., as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, etc. Preferably, ingredients should be approved by the U.S. Environmental Protection Agency for the use intended.

The methods of making such compositions are well known. Solutions are prepared by simply making the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration", Chemical Engineering, Dec. 4, 1967, pp. 147ff. and "Perry's Chemical Engineer's Handbook", 4th Edn., McGraw-Hill, New York, 1963, pp. 8-59ff.

For further information regarding the art of formulation, see for example:
- J. B. Buchanan, U.S. Pat. No. 3,576,834, Apr. 27, 1971, Col. 5 Line 36 through Col. 7 Line 70 and Examples 1-4, 17, 106, 123-140.
- R. R. Shaffer, U.S. Pat. No. 3,560,616, Feb. 2, 1971, Col. 3 Line 48 through Col. 7 Line 26 and Examples 3-9, 11-18.
- E. Somers, "Formulation", Chapter 6 in Torgeson, "Fungicides", Vol. I, Academic Press, New York, 1967.

FORMULATION EXAMPLE A

| Wettable Powder | |
|---|---|
| O,O—diethyl O—(5-phenylisozazol-3-yl)phosphorothioate | 20% |
| Methyl 2-(dimethylamino)-N—[[(methylamino)carbonyl]oxy]-2-oxoethanimidothioate | 10% |
| Sodium alkylnaphthalenesulfonate | 2% |
| Low viscosity methyl cellulose | 2% |
| Diatomaceous earth | 66% |

The ingredients are blended, coarsely hammer-milled and then air milled to produce particles of active essentially all below 10 microns in diameter. The product is reblended before packaging.

FORMULATION EXAMPLE B

| Wettable Powder | |
|---|---|
| O,O—diethyl O—(5-phenylisoxazol-3-yl)phosphorothioate | 25% |
| Methyl N—[[(methylamino)carbonyl]oxy]-ethanimidothioate | 15% |
| Dioctyl sodium sulfosuccinate | 1.5% |
| Sodium ligninsulfonate | 3% |
| Low viscosity methyl cellulose | 1.5% |
| Attapulgite | 54% |

The ingredients are thoroughly blended, passed through an air mill, to produce an average particle size under 15 microns, reblended and sifted through a U.S.S. No. 50 sieve (0.3 mm opening) before packaging.

All mixtures of compounds useful in the invention may be formulated in the same manner.

FORMULATION EXAMPLE C

| Wettable Powder | |
|---|---|
| O,O—diethyl O—(5-phenylisoxazol-3-yl)phosphorothioate | 30% |
| 2-Methyl-2-(methylthio)propionaldehyde O—methylcarbamoyloxime | 10% |
| Sodium alkylnaphthalenesulfonate | 2% |
| Low viscosity methyl cellulose | 2% |
| Diatomaceous earth | 56% |

The ingredients are blended, coarsely hammer-milled and then air milled to produce particles of active essentially all below 10 microns in diameter. The product is reblended before packaging.

FORMULATION EXAMPLE D

| Aqueous Suspension | |
|---|---|
| O,O—diethyl O—(5-phenylisoxazol-3-yl)phosphorothioate | 37.5% |
| Methyl N—[[(methylamino)carbonyl]oxy]-ethanimidothioate | 12.5% |
| Polyacrylic acid thickener | 0.3% |
| Dodecylphenol polyethylene glycol ether | 0.5% |
| Disodium phosphate | 1.0% |
| Monosodium phosphate | 0.5% |
| Polyvinyl alcohol | 1.0% |
| Pentachlorophenol | 0.4% |
| Water | 46.3% |

The ingredients are ground together in a sand mill to produce particles essentially all under five microns in size.

FORMULATION EXAMPLE E

| Oil Suspension | |
|---|---|
| O,O—diethyl O—(5-phenylisoxazol-3-yl)phosphorothioate | 18% |
| Methyl 2-(dimethylamino)-N—[[(methylamino)carbonyl]oxy]-2-oxoethanimidothioate | 7% |
| Polyoxyethylene sorbitol hexaoleate | 5% |
| Highly aliphatic hydrocarbon oil | 70% |

The ingredients are ground together in a sand mill until the solid particles have been reduced to under about 5 microns. The resulting thick suspension may be applied directly, but preferably after being extended with oils or emulsified in water.

FORMULATION EXAMPLE F

| Emulsifiable Concentrate | |
|---|---|
| O,O—diethyl O—(5-phenylisoxazol-3-yl)phosphorothioate | 20% |
| Methyl N—[[(methylamino)carbonyl]oxy]-ethanimidothioate | 10% |
| Blend of oil soluble sulfonates and polyoxyethylene esters | 4% |
| Xylene | 6% |
| Cyclohexane | 60% |

The ingredients are combined and stirred with gentle warming to speed solution. A fine screen is included in the packaging operation to insure the absence of any extraneous undissolved material in the product.

FORMULATION EXAMPLE G

| Emulsifiable Concentrate | |
|---|---|
| O,O—diethyl O—(5-phenylisoxazol-3-yl)phosphorothioate | 30% |
| Methyl 2-(dimethylamino)-N—[[(methylamino)carbonyl]oxy]-2-oxoethanimidothioate | 10% |
| Cyclohexane | 50% |
| Xylene | 6% |
| Sorbitan monostearate and polyoxyethylene condensates thereof | 4% |

The ingredients are combined and stirred to produce a solution which can be emulsified in water for application.

FORMULATION EXAMPLE H

| Granule | |
|---|---|
| Wettable Powder of Formulation Example C | 15% |
| Gypsum | 69% |
| Potassium sulfate | 16% |

The ingredients are blended in a rotating mixer and water sprayed on to accomplish granulation. When most of the material has reached the desired range of 1.0 to 0.42 mm. (U.S.S. #18 to 40 sieves), the granules are removed, dried, and screened. Oversize material is crushed to produce additional material in the desired range. These granules contain 6% active ingredient.

| Granule | |
|---|---|
| O,O—diethyl O—(5-phenylisoxazol-3-yl)-phosphorothioate | 7% |
| Methyl 2-(dimethylamino)-N—[[(methylamino)-carbonyl]oxy]-2-oxoethanimidothioate | 3% |
| Celatom MP-78 | 90% |

The ingredients are warmed to approximately 90° C. and sprayed upon dedusted and pre-warmed Celatom MP-78 granules in a double cone blender. The granules are then allowed to cool and are packaged.

FORMULATION EXAMPLE J

| Granule | |
|---|---|
| O,O—diethyl O—(5-phenylisoxazol-3-yl)-phosphorothioate | 7.5% |
| Methyl N—[[(methylamino)carbonyl]oxy]-ethanimidothioate | 2.5% |
| Attapulgite granules (low volatile matter, 0.71/0.30 mm; U.S.S. #25–50 sieves) | 90% |

The active ingredients are warmed to approximately 90° C. and sprayed upon dedusted and pre-warmed attapulgite granules in a double cone blender. The granules are then allowed to cool and are packaged.

FORMULATION EXAMPLE K

| High Strength Concentrate | |
|---|---|
| O,O—diethyl O—(5-phenylisoxazol-3-yl)phosphorothioate | 66% |
| 2-Methyl-2-(methylthio)propionaldehyde O—methylcarbomoyloxime | 33% |
| Trimethylnonyl polyethylene glycol ether | 1% |

The surfactant is added to the liquid mixture of the other two ingredients. The mixture is well blended. The concentrate may be formulated further for practical use.

FORMULATION EXAMPLE L

| Dust | |
|---|---|
| High Strength Concentrate, Example K | 25.4% |
| Pyrophyllite, powdered | 74.6% |

The ingredients are thoroughly blended and packaged for use.

What is claimed is:

1. A method of protecting plants from parasitic nematodes comprising applying to the locus of nematode infestation a plant protective amount of a mixture consisting essentially of:
    A. O,O-diethyl O-(5-phenylisoxazol-3-yl)-phosphorothioate, and
    B. at least one of:
        (1) methyl N-[[(methylamino)carbonyl]oxy]ethanimidothioate, and
        (2) methyl 2-(dimethylamino)-N-[[(methylamino)-carbonyl]oxy]-2-oxoethanimidothioate;
    the weight ratio of A to B being in the range of about 1:10 to about 10:1.

2. The method of claim 1 wherein the mixture applied is A and B(1).

3. The method of claim 1 wherein the mixture applied is A and B(2).

4. A method according to claim 1 or claim 2 or claim 3 wherein the weight ratio of A to B is within the range of about 2:1 to about 3:1.

* * * * *